United States Patent [19]

Fauss et al.

[11] Patent Number: 4,581,375
[45] Date of Patent: Apr. 8, 1986

[54] PESTICIDAL NOVEL SUBSTITUTED HYDROXYMALONIC ACID AMIDE-THIOAMIDES

[75] Inventors: Rudolf Fauss, Cologne; Kurt Findeisen, Odenthal; Benedikt Becker, Mettmann; Ingeborg Hammann, Muehlheim; Bernhard Homeyer, Leverkusen, all of Fed. Rep. of Germany

[73] Assignee: Bayer Aktiengesellschaft, Leverkusen, Fed. Rep. of Germany

[21] Appl. No.: 582,979

[22] Filed: Feb. 24, 1984

[30] Foreign Application Priority Data

Mar. 10, 1983 [DE] Fed. Rep. of Germany ....... 3308464

[51] Int. Cl.$^4$ .................... A01N 37/18; C07C 153/05
[52] U.S. Cl. ..................................... 514/599; 556/416; 556/417; 564/74; 558/408
[58] Field of Search ..................... 564/74, 78; 514/599

[56] References Cited

FOREIGN PATENT DOCUMENTS 0076957 4/1983 European Pat. Off. .
2533716 2/1976 Fed. Rep. of Germany .
3140275 4/1983 Fed. Rep. of Germany .

OTHER PUBLICATIONS

Helvetica Chimica Acta, Bd. 51, "Synthese und Eigenschaften . . . ", J. Kiss, Mar. 1968, pp. 235–339.

Primary Examiner—Dolph H. Torrence
Attorney, Agent, or Firm—Sprung Horn Kramer & Woods

[57] ABSTRACT

The present invention relates to new substituted hydroxy-malonic acid amide-thioamides of the formula (I)

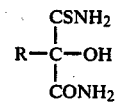

in which

R represents optionally substituted alkyl, optionally substituted alkenyl, optionally substituted cycloalkyl, optionally substituted aryl or optionally substituted heteroaryl, and a process for their preparation and their use as agents for combating pests, in particular insecticides and acaricides.

7 Claims, No Drawings

PESTICIDAL NOVEL SUBSTITUTED HYDROXYMALONIC ACID AMIDE-THIOAMIDES

The present invention relates to new substituted hydroxy-malonic acid amide-thioamides, a process for their preparation and their use as agents for combating pests.

It has already been disclosed that carbamates, such as 5,6-dimethyl-2-dimethylamino-4-pyrimidinyl dimethylcarbamate or 1-naphthyl N-methyl-carbamate, have insecticidal activity (U.S. Pat. Nos. 3,493,574 and 2,903,478). However, their action is not always completely satisfactory, especially when low concentrations are applied.

The new substituted hydroxy-malonic acid amide-thioamides of the formula (I)

in which
R represents optionally substituted alkyl, optionally substituted alkenyl, optionally substituted cycloalkyl, optionally substituted aryl or optionally substituted heteroaryl,
have been found.

It has furthermore been found that the substituted hydroxymalonic acid amide-thioamides of the formula I

in which
R represents optionally substituted alkyl, optionally substituted alkenyl, optionally substituted cycloalkyl, optionally substituted aryl or optionally substituted heteroaryl,
are obtained when hydroxy- or trimethylsilyloxy-carboxylic acid thioamide-nitriles of the general formula II

wherein
R has the abovementioned meaning and
X represents hydrogen or trimethylsilyl, are hydrolyzed with inorganic acids.

Surprisingly, the substituted hydroxy-malonic acid amide-thioamides according to the invention exhibit a considerably more powerful insecticidal action than the carbamates of the same type of action which are known from the prior art. The substances according to the invention are thus suitable for combating pests.

Compounds of the formula I in which
R represents $C_{1-4}$-alkyl, $C_{2-7}$-alkenyl or $C_{3-6}$-cycloalkyl, each of which is substituted by one or more identical or different radicals from the following group: halogen, in particular fluorine, chlorine or bromine, $C_{1-4}$-alkoxy in particular methoxy or ethoxy, carboxyl, carbalkoxy in particular methoxycarbonyl or ethoxycarbonyl, and phenyl, phenoxy and thiophenyl, it being possible for the phenyl rings to be substituted by halogen or alkyl; or
R furthermore represents phenyl, which is optionally substituted by one or more identical or different radicals from the following group: halogen, in particular chlorine, bromine or fluorine, nitro, amino, OH, CN, $C_{1-4}$-alkyl in particular methyl, $C_{1-4}$-halogenoalkyl in particular trifluoromethyl, trichloromethyl or pentafluoroethyl, $C_{1-4}$-alkoxy, $C_{1-4}$-halogenoalkoxy, in particular trifluoromethoxy or pentafluoroethoxy, methylenedioxy, ethylenedioxy, difluoromethylenedioxy, halogen-substituted ethylenedioxy, $C_{1-4}$-alkylthio, $C_{1-4}$-halogenoalkylthio in particular trifluoromethylthio, $C_{2-8}$-alkoxyalkyl, $C_{2-8}$-halogenoalkoxyalkyl, $C_{1-4}$-alkylsulphonyl in particular methylsulphonyl, $C_{1-4}$-halogenoalkylsulphonyl, carboxyl and carbalkoxy in particular methoxycarbonyl, or represents the radical $C_{1-4}$-alkoxy—N=CH—, in particular $CH_3$—O—N=CH—, or phenyl, phenoxy or thiophenyl, each of which can optionally be substituted by halogen, $C_{1-4}$-alkyl, or carbalkoxy with 2–4 C atoms, such as carbmethoxy, or
R furthermore represents heteroaryl, such as pyridinyl, pyrimidinyl, triazinyl, isoxazolyl, thiazolyl, oxadiazolyl, imidazolyl, triazolyl, furanyl or thienyl each of which can optionally be substituted by one or more identical or different substituents from the group comprising halogen in particular chlorine, $C_{1-4}$-alkyl, in particular methyl or ethyl, and $C_{1-4}$-alkoxy, in particular methoxy or ethoxy,
are preferred.

Compounds of the formula I in which
R represents $C_{1-4}$-alkyl or halogen- (in particular fluorine or chlorine)-phenyl- or -phenoxyl substituted $C_{1-4}$-alkyl or $C_{5-6}$-cycloalkyl, or $C_{1-4}$-alkenyl which is optionally substituted by carboxyl, or phenyl which is optionally substituted by halogen, in particular fluorine or chlorine, $C_{1-4}$-alkyl, in particular methyl, $C_{1-4}$-alkoxy, $C_{1-4}$-halogenoalkoxy, $C_{1-4}$-halogenoalkyl, $NH_2$, $CH_3O$—N=CH— or nitro,
are particularly preferred.

Compounds of the formula I in which
R represents phenyl which is optionally mono- or poly-substituted by chlorine or fluorine,
are very particularly preferred.

Specific new active compounds which may be mentioned are: phenyl-hydroxy-malonic acid amide-thioamide, o-, m- or p-chlorophenyl-hydroxy-malonic acid amide-thioamide, 2,3-dichlorophenyl-hydroxy-malonic acid amide-thioamide, 3,4-dichlorophenyl-hydroxymalonic acid amide-thioamide, 3,5-dichlorophenyl-hydroxymalonic acid amide-thioamide, 2,4-dichlorophenyl-hydroxy-malonic acid amide-thioamide, 2,5-dichlorophenyl-hydroxymalonic acid amide-thioamide, 2,6-dichlorophenyl-hydroxy-malonic acid amide-thioamide, 3,4,5-trichlorophenyl-hydroxymalonic acid amide-thioamide o-, m- or p-nitrophenyl-hydroxy-malonic acid amide-thioamide, o-chloromethyl-phenyl-hydroxy-malonic acid amide-thioamide, o-, m- or p-trifluoromethylphenyl-hydroxy-malonic acid amide-thioamide, o-, m- or p-methoxyphenyl-hydroxy-malonic acid amide-thioamide, 2,6-dimethoxyphenylhydroxy-malonic acid amide-thioamide, o-, m- or p-tolylhydroxy-malonic acid amide-thioamide, o-, m- or p-trifluoromethoxyphenyl-hydroxy-malonic acid amide-thioamide, o-, m- or p-fluorophenyl-hydroxymalonic acid amide-thioamide, cyclohexyl-hydroxymalonic acid amide-thioamide, benzyl-hydroxy-malonic acid amide-thioamide, butyl-hydroxy-malonic acid amide-thioamide, tert.-butyl-hydroxy-malonic acid amide-thioamide, fluoro-tert.-butyl-hydroxy-malonic acid amide-thioamide, chloro-tert.-butyl-hydroxy-malonic acid amide-thioamide, difluoro-tert.-butyl-hydroxy-malonic acid amide-thioamide and trichloromethyl-hydroxy-malonic acid amide-thioamide, 3,5-dichloro-4-methoxy-(or 4-hydroxy-) (or 4-amino)-phenyl-malonic acid-amide-thioamide.

If trimethylsilyloxyphenylmalonic acid thioamidenitrile is used as the starting substance and 96% strength sulphuric acid is used as the hydrolyzing agent, the course of the reaction can be represented by the following equation:

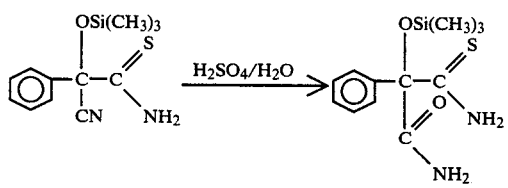

Water is generally used as the diluent for the hydrolysis. The hydrolysis can be carried out in anhydrous- or water-containing acids, and small amounts of water are frequently already sufficient to obtain the desired end products.

However, the amount of water can be varied within a substantial range, that is to say between 2% and 75%, based on the amount of acid employed. It is furthermore possible first to dissolve the starting substances of the formula II in an anhydrous acid and to add the required amount of water at a later point in time.

Preferred suitable acids which may be mentioned are: sulphuric acid, phosphoric acid, hydrochloric acid, hydrofluoric acid, perchloric acid and boric acid. Sulphuric acid ($H_2SO_4$) and hydrochloric acid (HCl) are particularly preferred.

In some cases, the end products of the general formula I are somewhat water-soluble and must therefore be removed from the water with the aid of an extracting agent. Possible extracting agents are all the inert organic solvents which are water-immiscible or only slightly water-miscible. These include toluene, xylene, chlorobenzene, dichlorobenzene, ethyl acetate, methylene chloride, chloroform, carbon tetrachloride and ether. In general, however, an extracting agent is not necessary.

The reaction temperatures can be varied within a substantial range. In general, the reaction is carried out between about −15° C. and 100° C., preferably between 0° and 80° C. and in particular between 20° and 60° C.

The reaction is usually carried out under normal pressure. However, it can also be carried out under increased pressure. In general, the reaction is carried out under pressures between about 1 bar and about 10 bar, preferably between 1 bar and 5 bar.

In carrying out the process according to the invention, about 0.5 to 20 moles, preferably 1 to 5 moles, of inorganic acid are employed per mole of the hydroxy- or trimethylsilyloxy-malonic acid thioamide-nitriles (formula II).

The compounds of the formula II dissolved in the acid is poured onto ice, after stirring for 30 minutes to two hours, and is isolated either by filtration with suction or extraction. Purification is in general effected by recrystallization.

In formula II, R is preferably straight-chain or branched $C_{1-6}$-alkyl, which is substituted by halogen, such as fluorine, chlorine or bromine, alkoxy or carbalkoxy groups, or, furthermore, preferably represents alkenyl radicals with 2 to 7 carbon atoms, which can be substituted by halogen, e.g. fluorine, chlorine or bromine, alkoxy, carboxyl or carbalkoxy groups, or, furthermore, preferably represents cycloalkyl radicals with 3 to 6 carbon atoms, which can be substituted by halogen, such as fluorine, chlorine or bromine, alkoxy or carbalkoxy groups, or R furthermore preferably represents aryl in particular phenyl, which can be substituted by alkyl with 1 to 4 carbon atoms, by alkyl wherein the substituents can be halogen, e.g. fluorine or chlorine, and alkoxy groups, by aryl, which furthermore can be substituted by halogen, such as fluorine, chlorine and bromine, $C_{1-4}$-alkoxy-, $C_{1-4}$-alkoxy which is substituted by chlorine or fluorine or $NH_2$ or nitro groups, or R furthermore preferably represents heteroaryl, which can be substituted by alkyl with 1 to 4 carbon atoms, alkoxy groups or halogen, e.g. fluorine, chlorine and bromine.

Compounds of the formula II are new.

They are obtained by a process in which (1) α-ketoacid thioamides of the general formula III

(III)

wherein

R has the abovementioned meaning, are reacted with HCN or agents which split off HCN, or trimethylsilyl cyanide, or (2) trimethylsilyloxymalonic acid dinitriles of the general formula IV

(IV)

wherein

R has the abovementioned meaning, are reacted with $H_2S$.

Process 1 may be illustrated by the following 3 equations:

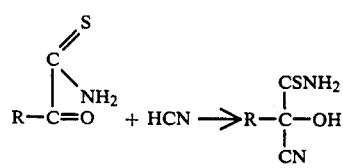

-continued $$R-\underset{\underset{NH_2}{|}}{\overset{\overset{S}{\parallel}}{C}}-C=O + (CH_3)_3SiCN \longrightarrow R-\underset{\underset{CN}{|}}{\overset{\overset{CSNH_2}{|}}{C}}-O-Si(CH_3)_3$$

$$R-\underset{\underset{NH_2}{|}}{\overset{\overset{S}{\parallel}}{C}}-C=O + CH_3-\underset{\underset{CN}{|}}{\overset{\overset{CH_3}{|}}{C}}-OH \longrightarrow R-\underset{\underset{CN}{|}}{\overset{\overset{CSNH_2}{|}}{C}}-OH + CH_3-\underset{}{\overset{\overset{CH_3}{|}}{C}}=O$$

Cyanohydrins can be used as the substances which split off HCN, and acetone cyanohydrin or benzaldehyde cyanohydrin may be mentioned as examples.

If phenylglyoxylic acid thioamide and trimethylsilyl cyanide are used as starting substances for the reaction, the course of the reaction can be represented by the following equation:

[Reaction of phenylglyoxylic acid thioamide with (CH$_3$)$_3$SiCN yielding product with OSi(CH$_3$)$_3$, CN, and C(S)NH$_2$ groups]

The reaction of III to give II proceeds by the methods known from the literature, in the presence of small amounts of alkaline catalysts, for example sodium cyanide, potassium cyanide or tertiary amines, such as triethylamine, as well as alkali metal and alkaline earth metal hydroxides and carbonates.

While the addition reaction of molar amounts of HCN or trimethylsilyl cyanide proceeds slightly exothermically even at room temperature and has ended when addition of the reagents has ended, if cyanohydrins are used, the mixture must be heated for some time in order to achieve complete conversion. In this case, it is also appropriate to add more than 1 mole of cyanohydrin per mole of α-ketothioamide of the formula XI. Preferably, 1.1–3, preferably 1.2–2, moles of cyanohydrin are used. The excess is distilled off again when the reaction has ended.

The reactions in general proceed in the absence of solvents, but it may in some cases be entirely appropriate to use solvents which are inert towards the products and educts, such as, for example, methanol, ethanol, isopropanol, toluene, chlorobenzene, methylene chloride, carbon tetrachloride and diethyl ether.

The reaction conditions for the reactions are very variable. Thus, for example, more than the stoichiometric amounts of HCN and trimethylsilyl cyanide can be employed, but more than a 10% molar excess brings no further advantages at all. The reaction temperature can likewise be varied within wide limits, and the reaction can be carried out in the temperature range from −50° to 300° C., the reactions either being carried out in the gas phase or in the liquid phase under pressure at the higher temperatures. In this case also, however, there is no significant advantage compared with the preferred experimental parameters initially described.

The addition of trimethylsilyl cyanide onto α-ketothioamides is surprising and cannot be predicted directly. Rather, because of the high silylation potential of the trimethylsilyl cyanide, N-silylation with splitting off of hydrocyanic acid would be expected.

Compounds of the general formula III are known, and they can easily be prepared by known processes (Ann. 691, 92 (1966)).

If 3,4-dichlorophenyltrimethylsilyloxymalonic acid dinitrile is used as the starting substance for the reaction with H$_2$S for process 2, the course of the reaction can be represented by the following equation:

[Reaction of 3,4-dichlorophenyltrimethylsilyloxymalonic acid dinitrile with H$_2$S]

The reaction proceeds by the process variant, known from the literature, for the preparation of α-keto-thioamides III.

It must be regarded as surprising here that only one of the two nitrile groups of the compound IV is selectively attacked by H$_2$S.

In general, the starting compound IV is dissolved in inert organic solvents and is reacted with hydrogen sulphide in the presence of alkaline catalysts. Examples of solvents which can be used are toluene, xylene, chlorobenzene and methylene chloride. The compounds mentioned for process 1 are used as catalysts, and the tertiary aliphatic amines, for example triethylamine, are preferred. They are employed in amounts of 0.01–5%, preferably 0.1–2%, based on the compound IV.

The reaction is carried out at temperatures from −30° to 40° C., preferably −10° to 30° C.

In general, H$_2$S is added to the trimethylsilyloxymalonic acid dinitrile with the catalyst in the solvent at about 0° C. At least the stoichiometric amount of H$_2$S, but advantageously an excess, must be used here. The mixture is then subsequently stirred at room temperature, during which the end product may already precipitate and then only have to be filtered off with suction. Otherwise, the mixture is concentrated and the product is then recrystallized.

Trimethylsilyloxymalonic acid dinitriles of the general formula IV are known (Chem. Ber. 106, 587 (1973), and Tetrahedron Letters No. 17, 1449–1450 (1973)).

New compounds can easily be synthesized by the methods described therein, in accordance with the following equation $$R-COCl + 2(CH_3)_3SiCN \longrightarrow R-\underset{\underset{CN}{|}}{\overset{\overset{CN}{|}}{C}}-OSi(CH_3)_3 + (CH_3)_3SiCl$$

wherein
R has the abovementioned meaning.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*.
From the order of the Diplopoda, for example, *Blani-*

*ulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium pyslloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp..

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic materials, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, such as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

EXAMPLE 1

3,4-Dichlorophenyltrimethylsilyloxymalonic acid thioamide-nitrile

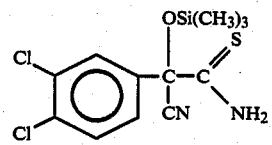

Process 2

2 ml of triethylamine were added to 120 g of 3,4-dichlorophenyltrimethylsilyloxymalonic acid dinitrile in 600 ml of absolute toluene, and dry H$_2$S was then passed in at $-5°$ C. Crystals thereby precipitated. After the mixture had been warmed to room temperature, the crystals were filtered off with suction and washed with a little toluene. 100 g of 3,4-dichlorophenyltrimethylsilyloxymalonic acid thioamide-nitrile were obtained by recrystallization from 700 ml of toluene. The substance had a melting point of 100°–128° C. and could not be completely freed from toluene.

Process 1

23.4 g of 3,4-dichlorophenylglyoxylic acid thioamide were suspended in 150 ml of absolute methylene chloride, 0.2 ml of triethylamine was added, and 10 g of trimethylsilyl cyanide were then slowly added at room temperature. A homogeneous solution was formed. The solvent was concentrated and the residue was recrystallized from toluene. 14 g of 3,4-dichlorophenyltrimethylsilyloxymalonic acid thioamide-nitrile remained. The substance had a melting point of 110°–116° C. and could not be completely freed from toluene.

EXAMPLE 2

3,4-Dichlorophenylhydroxymalonic acid amide-thioamide

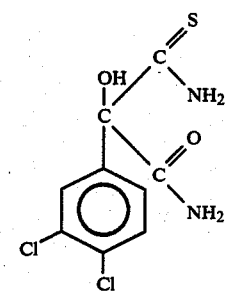

66.6 g of 3,4-dichlorophenyltrimethylsilyloxymalonic acid thioamide-nitrile were introduced into 300 ml of sulphuric acid at a maximum of 30° C. After one hour, the mixture was poured onto ice-water, the residue was filtered off with suction and taken up in CH$_2$Cl$_2$ solution, the mixture was extracted by shaking with NaHCO$_3$ solution and water and the organic phase was then extracted by stirring with active charcoal and worked up.

47.5 g of a highly viscous residue remained which, according to investigations by spectroscopy, predominantly consisted of the desired end product.

A small amount was filtered over silica gel (silica gel 60, Messrs. Merck; mobile phase: toluene/ethyl acetate 1:1). Pure 3,4-dichlorophenylhydroxymalonic acid amide-thioamide crystallized out of concentrated chloroform solution. Melting point: 104°–105° C.

EXAMPLE 3

Phenyltrimethylsilyloxymalonic acid thioamide-nitrile of melting point 143° C. (toluene) was prepared analogously to Example 1, Process 2. Yield: 80%.

EXAMPLE 4

Phenylhydroxymalonic acid thioamide-nitrile

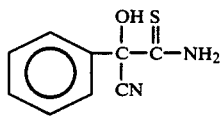

33 g of phenylglyoxylic acid thioamide were suspended in 250 ml of methylene chloride, 0.2 ml of triethylamine was added and a solution of 5.5 g of hydrocyanic acid in 15 ml of methylene chloride was added dropwise at 16° C. The solution became homogeneous and the end product then precipitated. After 1 hour, the precipitate was filtered off with suction, using a little methylene chloride containing a trace of toluenesulphonic acid. 22 g of phenylhydroxymalonic acid thioamide-nitrile remained; melting point: 110° C. (decomposition).

EXAMPLE 5

Phenylhydroxymalonic acid amide-thioamide

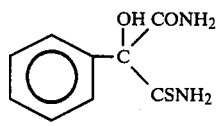

22 g of phenylhydroxymalonic acid thioamide-nitrile were introduced into 130 ml of $H_2SO_4$ at a maximum of 35° C. After 1 hour, the dark red solution was poured onto ice and the precipitate was filtered off with suction and washed thoroughly. For further purification, the procedure was as in Example 2. In this case also, the end product could not be obtained as crystals without separation over a silica gel column. The spectroscopic data (IR, NMR, MS (DCI)), however, confirmed its existence.

EXAMPLE A

Plutella test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the cabbage moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the following compound from the preparation examples shows a superior activity compared to the prior art: 2.

EXAMPLE B

Phaedon larvae test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the following compound from the preparation examples shows a superior activity compared to the prior art: 2.

EXAMPLE C

Tetranychus test (resistant)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compound from the preparation examples shows a superior activity compound to the prior art: 2.

EXAMPLE D

Test insects: *Phorbia antiqua* (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of the active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior activity compared with the prior art: 2 and 5.

It will be appreciated that the instant specification and examples are set forth by way of illustration and not limitation, and that various modifications and changes may be made without departing from the spirit and scope of the present invention.

We claim:

1. A substituted hydroxy-malonic acid amide-thioamide of the formula

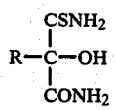

in which

R represents phenyl or halophenyl.

2. A compound according to claim 1, in which R is phenyl, which is optionally substituted by chlorine and/or fluorine.

3. A compound according to claim 1, wherein such compound is 3,4-dichlorophenylhydroxymalonic acid amide-thioamide of the formula

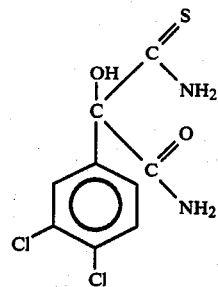

4. A compound according to claim 1, wherein such compound is phenylhydroxymalonic acid amide-thioamide of the formula

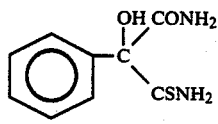

5. An insecticidal, arachnicidal or nematicidal composition comprising an insecticidally, arachnicidally or nematicidally effective amount of a compound according to claim 1 in admixture with a diluent.

6. A method of combating insects, arachnids or nematodes, which comprises applying to such insects, arachnids or nematodes or to a habitat thereof an insecticidally, arachnicidally or nematicidally effective amount of a compound according to claim 1.

7. The method according to claim 6, wherein such compound is
3,4-dichlorophenylhydroxymalonic acid amide thioamide, or
phenylhydroxymalonic acid amide-thioamide.

* * * * *